United States Patent [19]

Schneider et al.

[11] 4,085,153
[45] Apr. 18, 1978

[54] BROMINATION OF UNREACTIVE OLEFINS WITH BROMINE CHLORIDE

[75] Inventors: John A. Schneider; Jack F. Mills, both of Midland, Mich.

[73] Assignee: The Dow Chemical Company, Midland, Mich.

[21] Appl. No.: 466,097

[22] Filed: May 2, 1974

Related U.S. Application Data

[63] Continuation-in-part of Ser. No. 819,537, Apr. 24, 1969, abandoned.

[51] Int. Cl.$^2$ .............................................. C07C 25/00
[52] U.S. Cl. ........................... 260/649 R; 260/651 R; 260/653; 260/658 R
[58] Field of Search ............... 260/658 R, 653, 659 R, 260/660, 651 R, 649 R

[56] References Cited

U.S. PATENT DOCUMENTS

| | | | |
|---|---|---|---|
| 2,086,473 | 7/1937 | Nafash | 260/659 R |
| 2,124,426 | 7/1938 | McKee | 260/659 R |
| 2,374,933 | 5/1945 | Harding | 260/660 |
| 3,271,466 | 9/1966 | Peer | 260/660 |

FOREIGN PATENT DOCUMENTS

591,780  8/1947  United Kingdom ............ 260/658 R

OTHER PUBLICATIONS

"Unit Processes In Organic Synthesis," Groggins, 5th Ed., (1958), pp. 206–207.

*Primary Examiner*—Delbert E. Gantz
*Assistant Examiner*—Joseph A. Boska
*Attorney, Agent, or Firm*—E. E. Schillins; D. L. DeJoseph

[57] ABSTRACT

Bromine chloride is contacted with a normally unreactive olefin such as 1,2-di, tri- or tetrahalo- ethylene or 1,2-di, tri- or tetraphenyl ethylene or 1-halo-2-phenyl ethylene or 1-halo-2-phenyl ethylene carrying in addition, one or more other halogen or phenyl substituents on the carbons of the double bond in a two-phase, aqueous-organic reaction medium containing a bromide salt dissolved in the aqueous phase to produce the dibrominated adduct of the olefin. By the process of the invention, tetrachloroethylene was brominated to give a 77% yield of 1,2-dibromotetrachloroethane.

8 Claims, No Drawings

BROMINATION OF UNREACTIVE OLEFINS WITH BROMINE CHLORIDE

CROSS REFERENCE TO RELATED APPLICATION

This application is a Continuation-in-Part of our copending application Ser. No. 819,537 filed Apr. 24, 1969, now abandoned.

BACKGROUND OF THE INVENTION

The addition of bromine to olefins is well known. For the bromination of normally unreactive olefins such as di-, tri- or tetrahaloethylene or di-, tri- tetraphenyl ethylene with bromine in a conventional addition reaction, irradiation and other free-radial techniques have been employed. The yield of the dibrominated products by the use of such techniques, however, has been relatively low.

SUMMARY OF THE INVENTION

According to the invention, normally unreactive olefins carrying a halogen or a phenyl group on each carbon in the double bond are brominated by reacting the olefin with bromine chloride in the presence of a two-phase, aqueous-organic reaction medium containing an inorganic bromide salt dissolved in the aqueous phase.

By the process of the present invention, any olefin of the type described that is known to be unreactive in a conventional addition process using bromine may be reacted to form the dibromo adduct by the use of bromine chloride. Such olefins suitably include those which are normally unreactive due to the nature of the sustituents attached to each of the carbons of the carbon-carbon double bond such as 1,2-di-, tri- and tetrabromomethylene 1,2-di-, tri- and tetrachloroethylene, 1,2-di-, tri-, and tetrafluoroethylene, 1,2-di-, tri- and tetraiodoethylene, and those which are sterically hindered in the reaction such as the 1,2-di-, tri and tetraphenyl ethylene. Also suitable are 1-halo-2-phenyl ethylene or 1-halo-2-phenyl ethylene carrying, in addition, one or more other halogen or phenyl substituents on the carbons of the double bond. Of special interest in the present invention are tri- and tetrachloroethylene and tetrabromoethylene.

The bromine chloride used in the invention may suitably be prepared by mixing approximately equal molar amounts of bromine and chlorine in a closed container and drawing off the liquid contents to obtain a bromine chloride reactant of constant composition. After such removal, the bromine chloride may be used as a gas or a liquid.

The two-phase, aqueous-organic reaction medium of the present invention is formed by water and the olefin itself or any substantially inert hydrophobic organic solvent. The preferred organic solvents in the invention are the chlorinated lower alkanes such as methylene chloride, chloroform, carbon tetrachloride and ethylene dichloride. The relative amounts of the aqueous and organic phases in the reaction mixture are not critical. Any amount of the two phases may suitably be used so long as there is sufficient contact of the two phases to allow ion exchange between the aqueous and the organic layers.

The bromide salt dissolved in the aqueous layer of the solution may suitably be any bromide salt which is soluble in water. Of these soluble salts, the alkali metal, alkaline earth metal and ammonium bromides are preferred. The amount of bromide salt required is essentially a function of the amount of olefin and bromine chloride present.

The bromine chloride and olefin react in essentially equal molar amounts. Thus, an equal molar amount of the bromide salt must be present to provide the necessary bromine atom to form the dibromo adduct of the olefin. In the reaction, the bromine of the bromine chloride and bromide ion of the soluble bromide salt are added to the olefin and a chloride iron is formed. Although the three reactants react in essentially equal molar amounts, an excess of the olefin and bromide salt over the bromine chloride is preferred to avoid undesirable by-products.

In the preferred bromination process, a two-phase aqueous-organic reaction medium is prepared having the olefin constituting or dissolved in the organic phase and the bromide salt dissolved in the aqueous phase. Gaseous bromine chloride is then slowly introduced as finely divided bubbles into the reaction mixture, for example, by using a fritted glass or porous stone bubbler tube as the bromine chloride inlet, and the reaction mixture is slowly stirred. The addition and stirring are significant because slower bromine chloride addition and the slower stirring of the reaction mixture give greater yields of the dibromo adduct. The product formed is generally dissolved in the organic layer of the reaction mixture and may be separated by any conventional means, for example by distillation.

The reaction temperature may range from about 0° to 100° C or more with temperature below 50° C being preferred. Temperatures lower than 0° C reduce the rate of reaction to an impractically low level and temperatures above 100° decrease the yield of the dibromo adduct.

SPECIFIC EMBODIMENTS

EXAMPLES

A mixture of 83 grams (0.5 mole) of tetrachloroethylene, 40.6 grams (0.39 mole) of sodium bromide and 51 grams of water was prepared. The temperature of the mixture was maintained at 0° to 10° C as 37 grams (0.32 mole) of bromine chloride was slowly added with stirring. After all of the bromine chloride had been added, the mixture was stirred for 5 hours. The organic layer was washed in water and evaporated to yield 7.9 grams of 1,2-dibromotetrachloroethane for a yield of 11%.

Bromine chloride was reacted with tetrachloroethylene according to the procedure described above, but using different reaction conditions. In comparison runs under similar conditions, bromine was used in place of bromine chloride. The conditions and results of these examples and comparisons are summarized in Table I. Comparison run No. 3 compares the addition of $Br_2$ in the presence of chloride ion to show that the direction of $Br_2$ and $Cl^-$ is not analogous to the reaction of bromine chloride.

Examples 2 and 3 show different results for apparently identical reaction conditions. This difference is accounted for by the difference in the rate of addition of BrCl and the rate of stirring. The improved results of Example 3 were due to the slower rates of BrCl addition and stirring.

TABLE I

Bromination of Tetrachloroethylene

| Run No. | Brominating Agent | Solvent System | Temp. °C | Stirring | % Yield |
|---|---|---|---|---|---|
| Example 1 | BrCl+NaBr | H₂O+C₂Cl₄ | 0-10 | Fast | 8-11 |
| Comparison 1 | Br₂+NaBr | " | 0-10 | Fast | 1.1 |
| Example 2 | BrCl+KBr | " | 25 | Fast | 3.5 |
| Comparison 2 | Br₂+KBr | " | 25 | Slow | 0.8 |
| Example 3 | BrCl+KBr | " | 25 | Slow | 77 |
| Comparison 3 | Br₂+KCl | " | 25 | Slow | 3.8 |

In the same manner shown above, other normally unreactive olefins, such as tetrabromoethylene, tetrafluoroethylene, tetraiodoethylene trichloroethylene and 1,2-diphenylethylene, are reacted with BrCl in a two-phase, aqueous-organic reaction medium containing a soluble inorganic bromide to give respectively, hexabromoethane, 1,2-dibromo-1,1,2,2-tetrafluoroethane, 1,2-dibromo-1,1,2,2-tetraiodoethane, 1,2-dibromo-1,1,2-trichloroethane and 1,2-dibromodiphenylethane.

We claim:

1. A process for brominating the carbon atom pair connected by a double bond in an olefin in which each carbon of said carbon atom pair carries at least one substituent selected from the group consisting of fluorine, chlorine, bromine, iodine and phenyl, comprising reacting by contacting the olefin with bromine chloride in a two-phase, aqueous-organic reaction medium containing an inorganic bromide salt, selected from the group consisting of alkali metal bromide, alkaline earth metal bromide and ammonium bromide, dissolved in the aqueous phase, the organic reaction medium being selected from the group consisting of said olefin and a mixture of such olefin with an inert hydrophobic organic solvent.

2. The process defined in claim 1 wherein the unreactive olefin is 1,2-di-, tri- or tetrahaloethylene or 1,2-di-, tri- or tetraphenyl ethylene.

3. The process defined in claim 1 wherein essentially equal molar amounts of olefin, bromine chloride and bromide salt are reacted.

4. The process defined in claim 1 wherein a molar excess of olefin and bromide salt are reacted with bromine chloride.

5. The process defined in claim 1 wherein the bromine chloride is introduced as finely divided bubbles.

6. The process defined in claim 1 wherein the temperature is about 0° to 100° C.

7. The process defined in claim 1 wherein the temperature is 0° to 50° C.

8. The process defined in claim 1 wherein the olefin is tetrachloroethylene.

* * * * *

UNITED STATES PATENT AND TRADEMARK OFFICE
CERTIFICATE OF CORRECTION

PATENT NO. : 4,085,153
DATED : April 18, 1978
INVENTOR(S) : John A. Schneider et al.

It is certified that error appears in the above-identified patent and that said Letters Patent are hereby corrected as shown below:

Col. 1, line 14, delete "tri-tetraphenyl" and insert --tri- or tetraphenyl--.

Col. 1, line 16, delete "free-radial" and insert --free radical--.

Col. 1, line 35, delete "sustituents" and insert --substituents--.

Col. 2, line 12, delete "iron" and insert --ion--.

Col. 2, line 60, delete "direction" and insert --reaction--.

On the cover page, Col. 2, under other publications, delete attorney's name "E. E. Schillins" and insert --E. E. Schilling--.

Signed and Sealed this

Third Day of October 1978

[SEAL]

Attest:

RUTH C. MASON
Attesting Officer

DONALD W. BANNER
Commissioner of Patents and Trademarks